(12) United States Patent
Talman et al.

(10) Patent No.: US 7,704,755 B2
(45) Date of Patent: Apr. 27, 2010

(54) DIFFERENTIAL LABELLING METHOD

(75) Inventors: Eduard Gerhard Talman, Leiderdorp (NL); Robertus Petrus Maria van Gijlswijk, Alphen aan de Rijn (NL); Robert Jochem Heetebrij, Leiden (NL); Jacky Theo Maria Veuskens, Hasselt (BE)

(73) Assignee: Kreatech Biotechnology B.V., Amsterdam (NL)

( * ) Notice: Subject to any disclaimer, the term of this patent is extended or adjusted under 35 U.S.C. 154(b) by 1018 days.

(21) Appl. No.: 10/156,730

(22) Filed: May 28, 2002

(65) Prior Publication Data

US 2003/0060647 A1 Mar. 27, 2003

(30) Foreign Application Priority Data

May 28, 2001 (EP) ................................. 01202007

(51) Int. Cl.
*G01N 33/543* (2006.01)
*G01N 33/553* (2006.01)
*C07F 15/00* (2006.01)

(52) U.S. Cl. ........................ 436/525; 436/518; 556/136; 556/137

(58) Field of Classification Search ................ 435/4, 435/6, 7.1, 7.5; 436/518, 524, 525, 56, 106, 436/119, 163; 556/16
See application file for complete search history.

(56) References Cited

U.S. PATENT DOCUMENTS 5,175,256 A * 12/1992 Kasina et al. ............ 530/391.5
5,277,892 A * 1/1994 Rhodes ...................... 424/1.69
5,580,990 A 12/1996 van den Berg et al.
5,714,327 A 2/1998 Houthoff et al.

FOREIGN PATENT DOCUMENTS

| WO | 96/35696 | 11/1996 |
|---|---|---|
| WO | 98/15564 | 4/1998 |
| WO | 98/45304 | 10/1998 |
| WO | 00/27847 | 5/2000 |

OTHER PUBLICATIONS

Markus Hahn, et al., "Interaction of Cisplatin with Methionine- and Histidine-Containing Peptides: Competition between Backbone Binding, Macrochelation and Peptide Cleavage," *J. Biol. Inorg. Chem.* 6:556-566; (2001).
Andrei I. Ivanov, et al., "Cisplatin Binding Sites on Human Albumin," *The Journal of Biological Chemistry.* 273(24):14721-14730; (1998).
Mahmoud El-Khateeb, et al., "Reactions of Cisplatin Hydrolytes with Methionine, Cysteine, and Plasma Ultrafiltrate Studied by a Combination of HPLC and NMR Techniques," *Journal of Inorganic Biochemistry.*77:13-21; (1999).

(Continued)

*Primary Examiner*—Unsu Jung
*Assistant Examiner*—Leon Y. Lum
(74) *Attorney, Agent, or Firm*—Hoffmann & Baron, LLP

(57) ABSTRACT

The invention relates to a method for differentially labelling one or more entities, together comprising distinct reactive sites. The invention further relates to an entity that has been labelled by a method according to the invention and to a diagnostic kit comprising a labelled entity and to a diagnostic kit to employ a method according to the invention.

3 Claims, 6 Drawing Sheets

Adduct formation between Pt and N-Ac-Methionine at RT

OTHER PUBLICATIONS

Angelika Küng, et al., "Comparison of the Binding Behavior of Oxaliplatin, Cisplatin and Analogues to 5'-GMP in the Presence of Sulfur-Containing Molecules by Means of Capillary Electrophoresis and Electrospray Mass Spectrometry," *Journal of Inorganic Biochemistry*. 86:691-698 (2001).

Gordon Lowe, et al., "The Design and Synthesis of Bis-[4'-Azido-2,2':6',2"-Terpyridine Platinum(II)] Complexes with Rigid and Extended Linkers for Studying the Topology of DNA by Photoaffinity Labeling," *Bioorganic Chemistry*. 27:477-486 (1999).

Vicente Marchán, et al., "Towards a Better Understanding of the Cisplatin Mode of Action," *Chem. Eur. J.* 7(4):808-815 (2001).

Jan Reedijk, "Why Does Cisplatin Reach Guanine-N7 with Competing S-Donor Ligands Available in the Cell?," *Chem. Rev.* 99:2499-2510 (1999).

\* cited by examiner

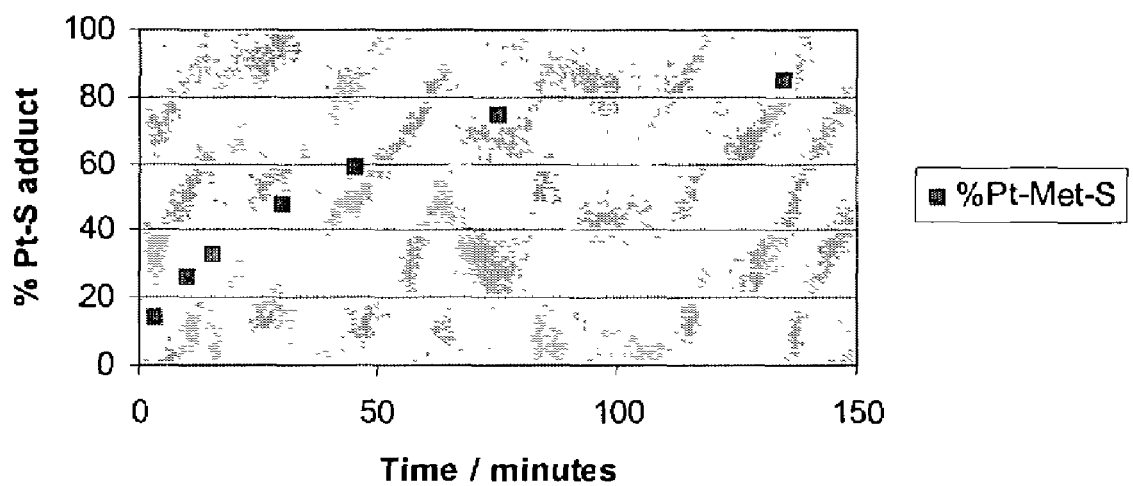
Fig. 1: Adduct formation between Pt and N-Ac-Methionine at RT

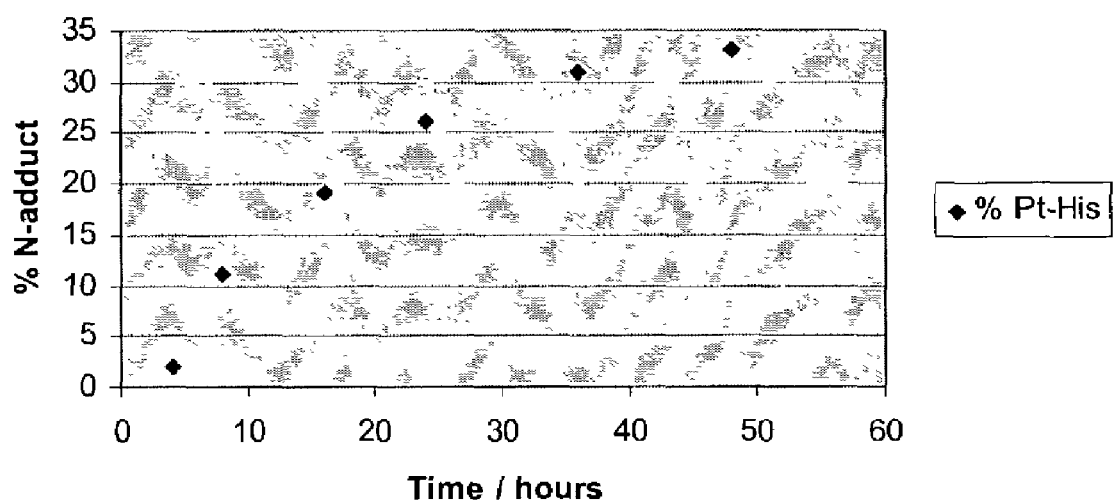
Fig. 2: Adduct formation between Pt and Histidine at RT

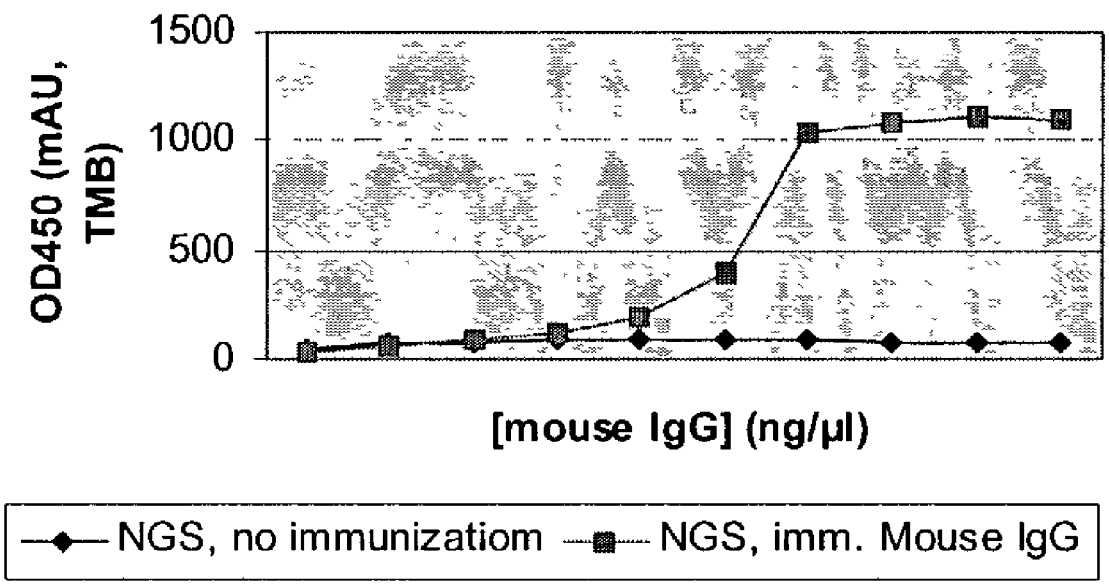
Fig. 3: Labeling of goat sera, non-immunized and immunized with mouse IgG. Mouse IgG coated/DNP-ULS labelled whole serum/anti-DNP-HRP detection

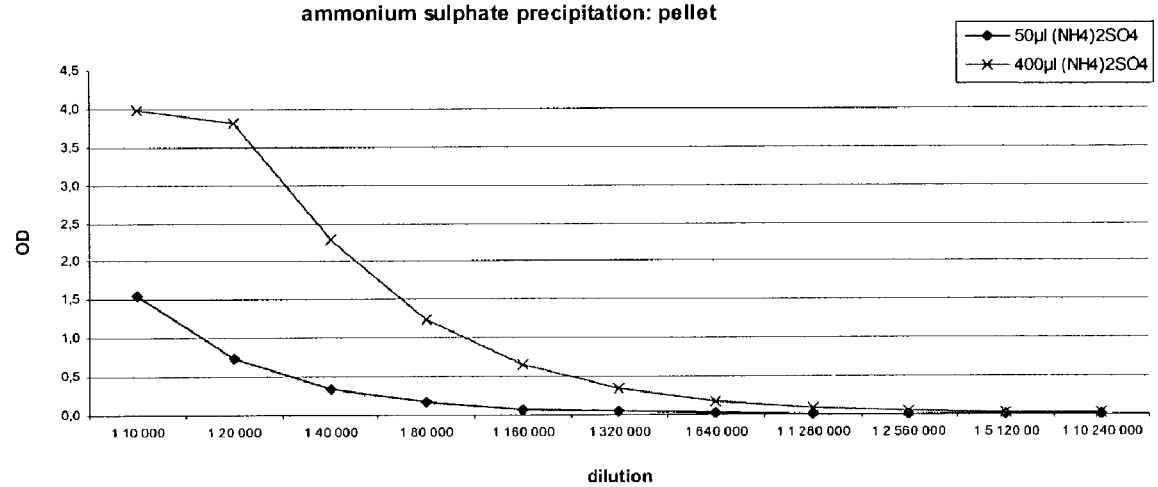
Fig. 4: labelling and detection of IgG serum proteins after ammonium sulphate precipitation: pellet

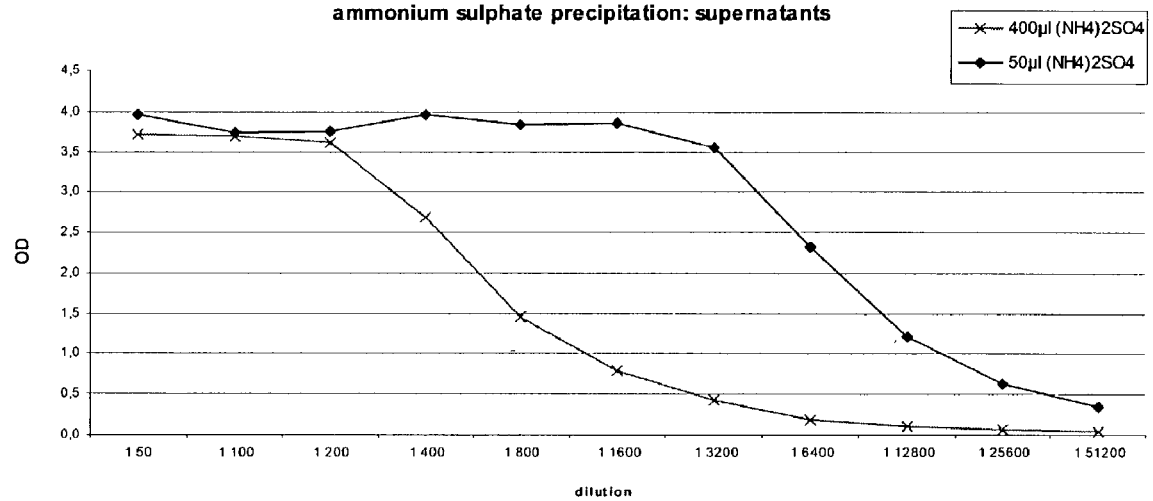
Fig. 5: labelling and detection of IgG serum proteins after ammonium sulphate precipitation: supernatants

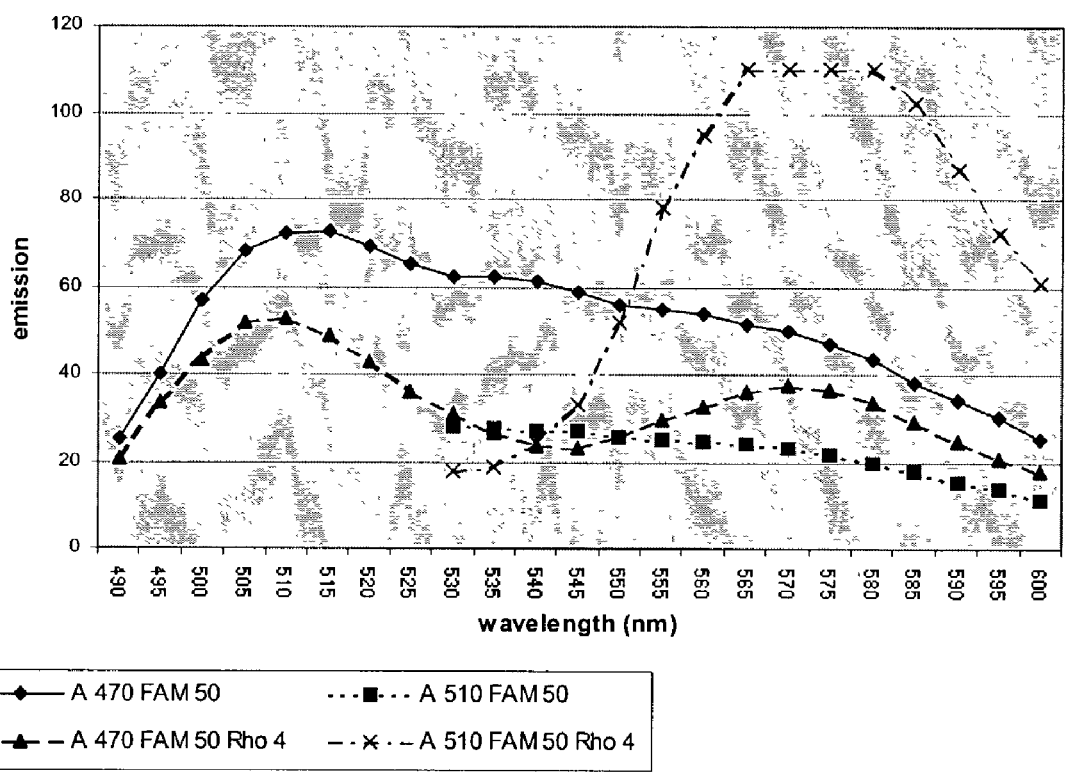
Fig. 6: mp-11 double labelling ic kit comprising entities differentially linked at one or more
DIFFERENTIAL LABELLING METHOD This application asserts the priority of European patent application 01202007.9 filed May 28, 2001, the contents of which are incorporated in their entirety herein by reference.

The invention relates to a method for differentially labelling one or more entities, together comprising distinct reactive sites, to an entity that has been labelled by a method according to the invention and to a diagnostic kit for employing a method according to the invention.

An entity may be labelled with a detectable marker to detect, visualise, quantify or monitor the entity e.g. in chemical, biological or medical research or diagnosis. A wide variety of labelling methods are known from the art (for a review see Hermanson, 1996, Bioconjugate techniques, Academic Press, ISBN 0-12-342335-X).

Many factors may play a role in choosing a particular detectable marker and a particular method of labelling. Such factors include the nature of the entity, reaction conditions, detection limits of the labelled entity, sensitivity during the labelling reaction and specificity towards the entity.

Methods using platinum compounds to label bio-organic molecules have been considered interesting for a very long time. Various types of detectable marker moieties can be adhered to ionic platinum. Platinum compounds may react with a variety of reactive moieties on an entity.

The use of a cis-platinum compound has been described in European patent application no. 95201197.1. Herein a method is disclosed for linking bio-organic molecules and markers through cis-platinum compounds, of which two co-ordination sites are occupied by two ends of a stabilising bridge, such as an ethylenediamine group. These known cis-platinum compounds are suitable for linking labels to several kinds of bio-organic molecules, such as peptides, polypeptides, proteins, and nucleic acids. Methods using trans-platinum compounds have also been reported (EP application 97201066.4) to be suitable to label a variety of bio-organic molecules.

The reactivity of platinum compounds towards a variety of reactive sites is a benefit in many applications, since it may allow fast labelling reactions and an excellent sensitivity towards a wide variety of entities.

It may however be desired to direct the label to a specific reactive site of an entity, e.g. to improve the selectivity of the labelling. Also, pre-selected sites may be labelled in complex samples such as those samples comprising various types of bio-organic compounds. Differential or selective labelling often circumvents the need of sample purification and may be directed in such a way that targeted entities do not loose their native characteristics, e.g. 3D structure, activity, avidity, etc.

Furthermore it may be advantageous to label an entity at a controlled number of reactive sites. This may improve accuracy of the quantification and facilitate identification of a labelled entity. Such an improvement would be very valuable for various applications such as in the organochemical, biological or medical fields.

Moreover it is often a challenge in labelling chemistry to find a labelling method that does not affect the structure or the activity of an entity, e.g. of an enzyme, an immunoglobulin or a DNA-probe, to a high extent.

It is an objective of the present invention to provide a method to differentially label one or more entities together comprising distinct reactive sites, at a targeted reactive site.

SUMMARY OF THE INVENTION

In one embodiment, the invention relates to a method for differentially forming a complex of a platinum compound and one or more entities, said entities together comprising one or more sulphur-containing reactive sites and one or more nitrogen-containing reactive sites, wherein said platinum compound is reacted with said one or more entities such that substantially only sulphur containing reactive sites or substantially only nitrogen containing reactive sites are linked to said platinum compound.

In another embodiment, the invention relates to method for differentially labelling one or more entities through a platinum-linker, said entities together comprising one or more sulphur containing reactive sites and one or more nitrogen containing reactive sites, wherein a complex of a platinum compound and a marker is formed, and wherein said platinum compound is reacted with said one or more entities such that substantially only sulphur containing reactive sites or substantially only nitrogen containing reactive sites are linked to said platinum compound.

In another embodiment, the invention relates to an entity differentially linked to a platinum compound at one or more nitrogen containing reactive sites and/or one or more sulphur containing reactive. A marker is optionally attached to the platinum compound. The entity may, for example, be labelled with different markers at, respectively, nitrogen containing reactive sites and sulphur containing reactive sites.

In another embodiment, the invention relates to a diagnostic kit comprising entities differentially linked at one or more nitrogen containing reactive sites and/or one or more sulphur containing reactive sites to a platinum compound and a marker.

In another embodiment, the invention relates to a diagnostic kit comprising one or more preparations selected from the group consisting of platinum linkers and at least one preparation selected from the group consisting of buffers, transition metal ion preparations, preparations for adjusting the ionic strength and preparations comprising a shielding moiety.

BRIEF DESCRIPTION OF THE FIGURES

FIG. 1 shows adduct formation between Pt and N-Ac-methionine at RT.

FIG. 2 shows adduct formation between Pt and histidine at RT.

FIG. 3 shows labelling of goat sera, non-immunized and immunized with mouse IgG. Mouse IgG coated/DNP-ULS labelled whole serum/anti-DNP-HRP detection.

FIG. 4 shows labelling and detection of IgG serum proteins after ammonium sulphate precipitation: pellet.

FIG. 5 shows labelling and detection of IgG serum proteins after ammonium sulphate precipitation: supernatants.

FIG. 6 shows mp-11 double labelling.

DETAILED DESCRIPTION OF THE INVENTION

Surprisingly, it has been found that, in accordance with one embodiment of the invention, one or more entities can be differentially labelled through a platinum-linker. In a preferred embodiment, said entities together comprise one or more sulphur containing reactive sites and/or one or more nitrogen containing reactive sites, wherein, optionally, a complex of a platinum compound and a marker is formed, and wherein said platinum compound is reacted with said one or more entities. By "together comprise one or more sulphur containing reactive sites and/or one or more nitrogen containing reactive sites" is meant that N- or S-reactive sites are both on the same entity, or that N-reactive sites are on one entity, and S-reactive sites are on another entity, as will be described in more detail below. In a preferred embodiment of the invention, substantially only sulphur containing reactive sites or substantially only nitrogen containing reactive sites are linked to said platinum compound.

Entity as used herein is to be interpreted as something that comprises one or more sulphur containing reactive sites and/or one or more nitrogen containing reactive sites. In particular an entity relates to an inorganic or organic compound, including a bio-organic compound. A bio-organic compound as used herein refers to a biological carbon containing compound. Also, a bio-organic compound refers to a compound capable of inducing or affecting an action in a biological system, e.g. by inducing or affecting a therapeutic or prophylactic effect, an immune response, a metabolic process etc. "Entity" further relates to a micro-organism, a virus or a prion, or to a material comprising one or more of said sulphur reactive or nitrogen reactive types of reactive sites, or a product made thereof, such as a micro-array, a microtitre plate, a test strip or a test tube. Distinct reactive sites—which ate to be labelled differentially—may be present together in one entity or in a combination (a mixture, a solution, a dispersion etc.) of entities having only one or some of the reactive sites to be labelled, but together comprising said distinct reactive sites. Such a combination is for example a combination of an entity with only a nitrogen containing reactive site and an entity with only a sulphur containing reactive site.

In principle, any type of nitrogen containing reactive site or sulphur containing reactive site may be labelled using a method according to the invention. Preferred reactive sites include reactive sites comprising a primary amine, a secondary amine, a tertiary amine, an aromatic amine, a thiol, a thioether, a sulfide, a disulfide, a thioamide, a thion, an amide, an imide, an imine, an iminoether, or an azide. Examples of entities that can be labelled are entities chosen from the group of amino acids (preferably methionine, cysteine, histidine, lysine, and tryptophan), peptides, oligopeptides, polypeptides, proteins, immunoglobulins, enzymes, synzymes, phospholipides, glycoproteins, nucleic acids, nucleosides, nucleotides, oligonucleotides, polynucleotides, peptide nucleic acids, peptide nucleic acid oligomers, peptide nucleic acid polymers, amines, aminoglycosides, nucleopeptides, and glycopeptides. Preferably in accordance with the invention, the entity is chosen from the group of amino acids, peptides, oligopeptides and polypeptides.

An entity linked to a platinum compound may be referred to as a Pt—S adduct (when attached to a sulphur containing reactive site), as a Pt—N adduct (when attached to a nitrogen containing reactive site), or in general as a Pt-adduct.

A sulphur containing reactive site may hereafter be referred to as an S-reactive site, and a nitrogen containing reactive site may hereafter be referred to as an N-reactive site.

A platinum linker is a platinum moiety that can be used to couple a marker to an entity. A preferred linker compound as used in this invention is a platinum compound to which ligands are bound.

It has been found that a method according to the invention is highly suitable to direct the labelling of an entity towards a specified reactive site within an entity or a group of entities that together comprise a variety of reactive sites. Furthermore a method according to the invention has been found to have excellent sensitivity towards the targeted (reactive site of the) entity, even in complex matrices. The prowess of a method according to the invention to distinguish to which reactive site a marker is labelled is inter alia extremely beneficial for analytical purposes. Not only may the excellent selectivity contribute to the accuracy and the dynamic range of quantification, but it also may improve the homogeneity of the labelled entity. The improved homogeneity generally has a beneficial effect upon band broadening during separation of a sample for analysis or for purification, e.g. by a chromatographic or electrophoretic method.

Furthermore it has been found possible to selectively label an entity without significantly affecting the structure or activity of the labelled entity, even if such an entity contains a fragile or labile part. This is a highly advantageous feature of the invention since it facilitates the detection or monitoring of a labelled entity while the entity retains activity—preferably substantially all of its activity—in vivo or in vitro. To the benefit of retaining activity, it has been found possible to direct labelling of an entity, such as an immunoglobulin, an enzyme, a hormone, or a nucleic acid in such a way that essentially no marker is labelled at one or more N- or S-reactive sites at a functional part of said entity.

Furthermore it was found that the present invention can be used to label an entity in such a way that the configuration of the entity largely remains unaffected after the entity has been labelled. This embodiment of the invention is for example particularly suitable for labelling an antibody-antigen complex or a double stranded oligo- or polynucleotide without disturbing the complex. This aspect of the invention may also be very useful for visualisation of the entity and/or certain chemical or biochemical processes in vivo or in vitro.

Examples of preferred platinum compounds are cis- or trans-platinum compounds of the formula $[Pt(II)(X_1)(X_2)(A)(D)]$ or a cis-platinum compound of the formula $[Pt(II)(X_3)(A)(D)]$.

Herein, Pt represents platinum (Pt), A and D represent the same or different reactive moieties, respectively involved in the complexation of the platinum compound to a marker and the linking of the platinum compound to the entity. The entities, $X_1$ and $X_2$ represent the same or different inert moieties, and $X_3$ represents an inert moiety that may act as a stabilising bridge, e.g. a bidentate ligand.

A structural representation of some examples of such platinum compounds is shown below:

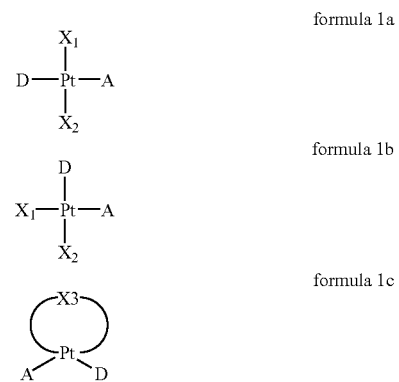

formula 1a formula 1b formula 1c

A platinum(II) compound, for use in a method of the invention can be prepared via any method known in the art. References can for example be found in Reedijk et al (Structure and Bonding, 67, pp. 53-89, 1987). The preparation of some trans-platinum compounds is disclosed in EP-A 97201066.4. Further preparation methods can be found in EP-A 96202792.6 and EP-A 95201197.1. Methods described in any of these publications are incorporated herein by reference. In a preferred embodiment of the invention platinum compounds are prepared according to the spacer-tert butoxycarbonyl/NHS-label pathway.

The reactive moieties (A, D) of a platinum compound are preferably good leaving ligands. A platinum compound, wherein A and/or D are independently chosen from the group of $Cl^-$, $NO_3^-$, $HCO_3^-$, $CO_3^{2-}$, $SO_3^{2-}$, $ZSO_3^-$, $I^-$, $Br^-$, $F^-$, acetate, carboxylate, phosphate, oxalate, citrate, a phosphonate, $ZO^-$, and ater has been found to be particularly suitable for use in a method according to the invention. Z is defined herein as a hydrogen moiety or an alkyl or aryl group having from 1 to 10 carbon atoms. Of these ligands, $Cl^-$ and $NO_3^-$ are most preferred.

Any type of inert moiety may be chosen. Inert as used herein indicates that the moiety remains attached to the platinum compound during the labelling process and thereafter without chemically reacting with an entity. A platinum compound comprising one or two inert moieties chosen from the group of $NH_3$, $NH_2R$, $NHRR'$, $NRR'R''$ groups, wherein R, R' and R'' preferably represent an alkyl group having from 1 to 6 carbon atoms have been found to be particularly suitable for use in a method of the present invention. $H_2NCH_3$ is a particularly preferred inert moiety for use in a method according to the invention. An alkyl diamine, wherein the alkylgroup has 2 to 6 carbon atoms is a preferred bidentate inert moiety in a cis-platinum compound (e.g. X3 in formula 1c). In a particularly preferred embodiment X3 represents ethylene diamine.

Preferred platinum compounds for use in a method according to the invention include cis[Pt(en)Cl$_2$], cis[Pt(en)Cl(NO$_3$)], cis[Pt(en)(NO$_3$)$_2$], trans[Pt(NH$_3$)$_2$Cl$_2$], trans[Pt(NH$_3$)$_2$Cl(NO$_3$)], and trans[Pt(NH$_3$)$_2$(NO$_3$)$_2$].

The term labelling is used herein to refer to connecting a marker with an entity, possibly via a platinum linker. A marker as used herein may be any moiety that can be attached to the platinum compound or the entity, and that can be used to detect, monitor or visualise the entity. A marker may be reacted with the platinum compound at any time. Hence, in accordance with the invention it is possible that a platinum linker is first reacted with a marker to obtain a linker-marker complex, which is then reacted with the entity. It is also possible that the order is reversed, i.e. by first linking the platinum compound, typically through a coordinate bond, selectively to an S-reactive site or to an N-reactive site of the entity to form a linker-entity complex. The linker-entity complex may then be bonded to a marker. In a preferred embodiment, the platinum linker is first reacted with the marker.

Any type of marker may be used as long as it can be attached to the platinum compound. Such a marker may be a radioactive marker, an enzyme, a specific binding pair component such as avidin, streptavidin or biotin, biocytin, iminobiotin, a colloidal dye substance, a phosphorescent marker (e.g. an Europium chelate, a platinum porphyrin), a chemiluminescent marker (e.g. luminol), a fluorochrome, including a cyanine, an Alexa dye (Molecular Probes), or Bodipy-colourant (Molecular Probes), a rhodamine, dinitrophenol (DNP), carboxyrhodamine, tert-butoxycarbonyl, a reducing substance (eosin, erythrosin, etc.), a (coloured) latex sol, digoxigenin, a metal (ruthenium), a metal sol or another particulate sol (selenium, carbon and the like), dansyl lysin, a UV dye, a VIS dye, Infra Red Dye, coumarine (e.g. amino methyl coumarine), an antibody, protein A, protein G, etc.

Particular preferred are DNP, fluorescein, cyanine-colorants and tetramethylrhodamine, inter alia because they can form stable complexes with platinum linked to an entity and they may give rise to excellent limits of detection. These markers can very suitably be used for a technique referred to as multi-colour labelling. Thus several colorants of this kind, optionally having similar chemical structures while having different colours, may be used. Other preferred markers include biotin, avidin, streptavidin and digoxygenin.

In an embodiment of the invention the marker and/or a reactive site of the entity may be connected to platinum through a spacer. Preferably such a spacer comprises a chain having at least four atoms, and preferably not more than 20 atoms, which chain comprises an electron donating moiety on one end and a moiety for reacting with a marker or an entity on the other end, wherein the chain is attached to platinum through the electron donating moiety. Of course, the spacer(s), the marker, the entity and the platinum linker may be attached to each other in any order. For instance, the spacer(s) may first be attached to the linker followed by reacting the obtained compound with a marker and the entity. It is also possible first to attach the spacer(s) to the marker before the reaction with the linker. The electron donating moiety of the spacer may for example be an amino group or a thiolate anion. Preferably, the chain comprises carbon atoms. More preferably, the chain further comprises at least one heteroatom. Heteroatoms include, for example, N (e.g. —NH—, —O—, and S). Highly preferred spacers are 1,6-diaminohexane and 1,8-diamino-3,6-dioxaoctane. In a preferred embodiment of the invention use is made of 1,6-diaminohexane tert-butoxycarbonyl, as an intermediate linker-spacer complex, prior to attaching to a marker and/or entity. It goes without saying that the labelling complex may contain more than one platinum, e.g. two platinum atoms, such as for example described in European Patent Application 97201066.4.

One of the reaction parameters that have been found particularly useful to choose such that an entity is differentially labelled in a method according to the invention, is the pH value. The pH as used herein should be interpreted as the pH value of a composition or product according to the invention in water at 20° C. In case an embodiment of the invention is employed in an environment leading to an altered solvent autoprotolytic constant ($pK_w$), (e.g. presence of organic solvents, altered temperature) a pH mentioned herein should be interpreted based upon the pH range at 20° C. in water.

In general, the formation of Pt—S adducts is pH independent whereas formation of Pt—N adducts is pH dependent. In a preferred embodiment one or more S-reactive sites are selectively labelled over one or more nitrogen containing sites by making use of the pH.

As a guideline, in a preferred embodiment, one may choose the pH of the invention at a pH below the lowest pKa of any of an entity's N-reactive sites that should not be labelled, allowing differential labelling of one or more S-reactive sites. As the skilled professional will understand, besides pKa, other factors may play a role, including the influence of the micro-environment in the vicinity of an entity that is to be labelled.

In a preferred embodiment the S-reactive site or sites are selectively labelled at a neutral or acidic pH. In a more preferred embodiment the S-reactive site or sites are differentially labelled over N-reactive sites at a pH of 5 or less.

It has also been found possible to label histidine residues distinctively over other N-reactive sites at a pH between about 6 and 8. A residue of a compound as used herein should be interpreted as the compound itself or as part of a larger entity, e.g. an amino acid residue in a protein.

An overview on the formation of Pt—S and Pt—N adducts at various pH values is given in Table 1.

TABLE 1 pH dependent formation of Pt-S and Pt-N adducts in proteins

|  | pH > 10 | pH = 7 | pH < 5 |
|---|---|---|---|
| S donor(s) | all | all | all |
| N donor(s) | all | Histidine only | none |

The presence of ions may also be used to control the selectivity of the platinum compound for N-reactive sites. In an embodiment, one or more leaving ligands, preferably anionic moieties, are used in the inhibition of linking or labelling a platinum compound to an N-reactive site, in order to enhance differentiated linking or labelling of an S-reactive site. Examples of such leaving ligands include $Cl^-$, $NO_3^-$, $HCO_3^-$, $CO_3^{2-}$, $ZSO_3^-$, $SO_3^-$, $I^-$, $Br^-$, $F^-$, acetate, carboxylate, phosphate, nitrate, oxalate, citrate, a phosphonate, $ZO^-$, and water. Z is defined herein as a hydrogen moiety or an alkyl or aryl group having from 1 to 10 carbon atoms. Alkyl or aryl group having from 1 to 10 carbon atoms include, for example, methyl, ethyl, phenyl, or benzyl. Particularly good results have been achieved by using salts comprising an anionic moiety, of which chloride is particularly preferred. The counter ions are preferably alkali metal cations, alkaline earth metal cations or cations also used to direct the labelling. In a preferred embodiment the total ionic strength of said anionic moieties used in the inhibition of labelling to an N-reactive site is at least 0.1 mol/l or at least about 0.5 mol/l. More preferably the total ionic strength is in the range of 0.1 to 0.5 mol/l.

The presence of metal ions, such as transition metal ions, may also be used for selection of the reactive site to be labelled. In particular, such ions have been found suitable to prevent or slow down labelling of an S-reactive site or to make a labelled Pt—S adduct labile, so that effectively one or more N-reactive sites are differentially labelled over said S-reactive site. Within a method according to the invention, it is also possible to direct the labelling by making use of geometrical isomers of a platinum compound—e.g. a cis-platinum compound and a trans-platinum compound,—such that the platinum compound is specifically labelled to either a sulphur containing reactive site or to a nitrogen containing reactive site.

The presence of a bulky inert moiety at the platinum compound may for example be used to prevent labelling at a reactive site of an entity, wherein said reactive site is partially shielded from a platinum compound with a particular stereochemical structure by the structure of the entity. This may for example be the case if the entity has a complex 3D structure, e.g. a protein, a conglomerate of molecules, etc.

It is also possible to differentially label an entity according to the invention by first shielding with a shielding moiety one or more reactive sites of the entity that should not be linked to, or labelled with, a platinum compound, and thereafter reacting a targeted reactive site of the entity with the platinum compound to which a marker either is or is not attached.

Shielding as used herein is to be interpreted as deactivation of the affinity of a reactive site of an entity for a platinum compound or for a marker, i.e. a platinum linker-marker complex, by reaction of the reactive site with a moiety that prevents attachment of the platinum compound or of the marker directly to said reactive site, or complexation of a marker with platinum linked with the reactive site. Preferably the shielding moiety is present in excess over the number of reactive sites that are to be shielded. The preferred reaction time for the shielding process will depend upon the application, and it will be clear to the skilled professional how to choose the reaction conditions.

In another preferred embodiment the shielding moiety is selectively removed from the shielded reactive site, after the platinum compound has been reacted such that said platinum compound is differentially linked to said entity.

In a preferred embodiment, one or more S-reactive sites may be shielded, e.g. by a trans-platinum compound, under conditions as described above, prior to selectively labelling one or more N-reactive sites of one or more entities. Particularly good results have been achieved with Rhodamine trans-Pt (trans[Pt(II)$(NH_3)_2$($NH_2$—$(CH_2)_6$—NH-rhodamine)Cl]($NO_3$)) as the shielding moiety. To improve shielding even further, the reaction was performed at a pH chosen between 2 and 5, after which the pH was increased to an alkaline pH for labelling N-reactive sites. Other preferred shielding compounds are cadmium, mercury, zinc or palladium complexes, such as, for example, Cd(acatate)$_2$; CdBr$_2$; CdCl$_2$; CdI$_2$; CdCO$_3$; Cd(OH)$_2$; Cd(NO$_3$)$_2$; CdSO$_4$; Hg(acatate)$_2$; HgBr$_2$; HgCl$_2$; HgI$_2$; Hg(NO$_3$)$_2$; HgSO$_4$; K$_2$HgI$_4$; Zn(acatate)$_2$; ZnBr$_2$; ZnCl$_2$; ZnI$_2$; Zn(NO$_3$)$_2$; ZnSO$_4$; Zn(OOCCF$_3$)$_2$; Zn(SO$_4$)$_2$; Pd(acatate)$_2$; PdBr$_2$; PdCl$_2$; PdI$_2$; PD(OH)$_2$; Pd(NO$_3$)$_2$; PdSO$_4$; PdC$_2$O$_4$.

The addition of transition metal ions, such as Cu(II), Zn(II) or a mixture thereof has been found to be particularly suitable to selectively remove a trans-platinum compound from an S-reactive site, whilst a labelled N-reactive site of a Pt-adduct substantially remains stable.

The type of solvent may also be used to differentiate the labelling. In particular the reactivity towards N-reactive sites can vary depending upon the solvent. In particular solvents that may act as a ligand to the platinum compound may decrease the reactivity towards N-reactive sites, and thus such a solvent may favour the labelling of S-reactive sites.

In addition to the parameters as mentioned above, a method according to the invention may further be fine tuned by parameters such as temperature, preferably varied in the range between 0° C. and 120° C., more preferably in the range between 20° C. and 70° C.; reaction time, commonly in the range between 1 min and 48 hours, preferably in the range between 10 min and 24 hours, more preferably in the range between 25 min and 15 hours; concentration of the reagents, molar ratio of the reagents, overall net charge of the platinum labelling complex, and the like. These parameters may be adjusted depending upon the particular application in any way known in the art. The overall net charge of the platinum labelling complex, for example, affects the specificity of Pt—N adduct formation in histidine at neutral pH. Neutral Pt-complexes, such as fluorescein- and cyanine Pt complexes, form Pt—N adducts whereas positively charged platinum labelling complexes, e.g. rhodamine- and dinitrophenol Pt complexes, do not. Positively charged Pt labelling complexes display differential labelling towards N adducts above the isoelectric point of the peptide, protein, and the like. Apart from allowing the selective labelling of N-reactive sites over S-reactive sites or vice versa, a method according to the present invention also makes it possible to differentiate between distinct N-reactive sites or distinct S-reactive sites, by choosing the correct conditions, such as described herein.

For example, one or more N-reactive sites of histidine residues may be labelled differentially over one or more other N-reactive sites by linking a platinum compound with a marker, and choosing the reaction conditions such that said platinum compound is differentially linked to a histidine residue of said entity. Such a method can be employed in the presence of S-reactive sites—which may be shielded during the labelling of histidine—but also in the absence thereof.

Thus an entity, such as a peptide or a protein, can be selectively labelled at one or more histidine residues in a mixture of amino acids or other N-reactive site containing entities. In a preferred embodiment differentially labelling of histidine is accomplished by choosing a pH of about 7 and a Pt labelling complex, with an overall neutral charge.

The selective labelling of a particular type of S-reactive site or a particular type of N reactive site offers a solution in several application areas. It may for example be used to screen for a particular type of reactive site in a entity of unknown composition or the presence of a particular entity in a sample. (e.g. the presence of histidine in an amino acid mixture). Thus in a repeated differential labelling process, several entities can one after another be labelled with a different marker, which may be useful for screening of several components without requiring separation of a sample, e.g. by chromatography, electrophoresis and/or mass spectrometry.

It may also add further specificity towards the labelling in order to avoid labelling at an undesired reactive site (e.g. at a functional part of an entity).

Furthermore discrimination between distinct N-reactive sites or distinct S-reactive sites, allows the creation of an entity with a multitude of different markers.

With a method according to the invention one or more labelled entities can be prepared. The invention also relates to such entities, differentially linked with a platinum compound at an N-reactive site or an S-reactive site. The invention further relates to a labelled entity wherein a marker is attached to the entity via a platinum compound linked to a specific reactive site of the entity.

In a particular embodiment according to the invention, at least one other reactive entity is differentially or non-differentially linked to a platinum compound or labelled with a platinum compound-marker complex, after selective linking or labelling of a first reactive site of an entity or a mixture of entities. Such subsequent linking or labelling may take place with a different marker that is reacted with a platinum compound according to the invention, but it is also possible to use another type of linking or labelling reaction known in the art. For example, after differentially labelling an S-reactive site, a subsequent linking or labelling may take place with a linker or label that is reactive towards amines.

In a preferred embodiment subsequent labelling also involves differential labelling. Thus it is possible to prepare an entity to which different markers are labelled at distinct reactive sites.

Thus it has been found possible to label an entity or a mixture of entities with several of different markers. Accordingly, the invention relates to entities having two or even a plurality of markers. Labelling with more than one marker can be very useful in various applications. It may for example be used to screen for particular entities in a mixture, without needing an analytical separation, e.g. screening for the presence of methionine and histidine in an amino acid mixture. In another embodiment it may be used to monitor a process in which a labelled entity is involved, e.g. a process in which an entity is split into several entities, each having a different label or vice versa. It goes without saying that the invention is not restricted to qualitative analyses but also includes quantitative analyses of differential labelled entities. In principle, a labelled entity may be subsequently analysed using any liquid based analyte analysis system. In a particularly suitable method according to the invention, comprising the analysis of a labelled entity, the labelled entity is analysed using a high throughput screening liquid based multiple analyte analysis system, e.g. a flow cytometry system.

The present invention further relates to a diagnostic kit comprising an entity according to the invention. A diagnostic kit according to the invention preferably comprises entities differentially linked to a platinum compound at one or more nitrogen containing reactive sites and/or one or more sulphur containing reactive sites, and one or more preparations selected from the group consisting of platinum-linker preparations, buffers, marker preparations, transition metal ion preparations, preparations for adjusting the ionic strength and preparations comprising a shielding moiety.

In one embodiment, the diagnostic kit comprises entities differentially linked at one or more nitrogen containing reactive sites and/or one or more sulphur containing reactive sites to a platinum compound and a marker.

In another embodiment, the invention relates to a diagnostic kit comprising one or more preparations selected from the group consisting of platinum linkers and at least one preparation selected from the group consisting of buffers, transition metal ion preparations, preparations for adjusting the ionic strength and preparations comprising a shielding moiety.

Another embodiment of the invention relates to a diagnostic kit, for employing a method according to the invention. Such a kit may for example comprise reaction instructions, one or more platinum compounds for labelling the entity, one or more markers, one or more entities according to the invention, one or more test samples, one or more other reagents, one or more test tubes or strips and the like.

The invention will now further be illustrated by the following non-limiting examples.

Example 1

Two amino acids (histidine and methionine, 0.1 mmol each) were dissolved in 500 µl deuterated sodium phosphate buffer (50 mM, pD=7.00) and incubated at room temperature with a slight excess (0.44 mmol) of [Pt(en)(NH$_2$—NH-Boc)Cl](NO$_3$)$_3$(=PtN$_3$—Cl), wherein Boc is a marker ((en)=ethylenediamine, Boc=tert-butoxycarbonyl). The reaction process was monitored using high-resolution NMR (Bruker DPX-300) visualising $^1$H and $^{195}$Pt nuclei. The results are shown in FIGS. 1 and 2. The data showed almost completion of the reaction for the S-reactive sites (methionine, FIG. 1) within 120 min, demonstrated by change in signal from PtN$_3$—Cl to Pt N$_3$—S-adduct whereas the reaction between the N-reactive sites and the platinum compound proceeded slow (FIG. 2). After 24 hours only a quarter of the histidine molecules had been labelled.

Example 2

Bovine serum albumin (BSA) was dissolved in 0.5×PBS (phosphate buffered saline, pH=7.4) to a 1 mg/ml solution. To 1 ml sample of the BSA solution, 0.5 mg Rhodamine cis-Pt (cis[Pt(II)(en)(NH$_2$—(CH$_2$)$_6$—NH-rhodamine)Cl](NO$_3$)) was added. To another 1 ml sample of BSA solution, 0.5 mg Rhodamine trans-Pt (trans[Pt(II)(NH$_3$)$_2$(NH$_2$—(CH$_2$)$_6$—NH-rhodamine)Cl](NO$_3$)) was added. Both samples were allowed to react for 16 hrs at 37° C. Thereafter unbound fluorophores (unbound Rhodamine and unbound Rhodamine-Pt compound) were removed by gel filtration (10 ml Sephadex G50 column, 10 cm length, 1 cm diameter) using 1×PBS as an eluent. Next, the ratios of bound fluorophore per protein (F/P ratio) were determined using the following formula:

$$F/P \text{ ratio} = \frac{112.4 \times A521}{95.0 \times [BSA]}$$

wherein A521 (absorbance at 521 nm) was determined using a Ultrospec 4000 spectrophotometer (APB), and [BSA] (protein concentration in µg/µl was determined with BCA reagent (BCA protein assay kit nr. 23225, Pierce)

Platinum compound to protein ratios (Pt/P ratio) was determined using the following formula:

$$Pt/P \text{ ratio} = \frac{68{,}000 \times [Pt]}{195.0 \times [BSA]}$$

wherein [Pt] (platinum concentration in µg/l was determined by atomic absorption spectroscopy. Briefly, the extend of platinum-protein binding was determined by a Perkin Elmer Atomic Absorption Spectrometer 3100 set to a slitband of 0.70 nm to monitor the Pt line at 265.9 nm. The linear range for quantification was 100-1500 ng/mL. Deuterium background correction was used throughout analysis and the sample volume was between 0.020-0.060 mL. Furnace parameters were: drying 120° C./90 sec., ashing 1300° C./60 sec., flushing 20° C./15 sec. and atomization at 2650° C./5 sec. Argon gas was used to purge the furnace.

The results were as follows:

| Platinum compound | F/P ratio | Pt/P ratio |
|---|---|---|
| Cis | 4.1 | 4.0 |
| Trans | 0.9 | 3.6 |

BSA is rich in methionine and cystein residues (S-reactive sites), at the above conditions reaction to N-reactive sites is slow. The Pt/P ratio shows that both the cis and the trans-Platinum compound successfully react with the protein. The F/P ratio shows however that under the conditions of this experiment only the marker (rhodamine) is released from the trans-platinum compound, while the cis-platinum compound remains bound to the protein. This illustrates that a trans-platinum compound may be used to shield a reactive site from attachment of a marker to the trans-platinum bound reactive site.

Example 3

Bovine serum albumin (BSA, Sigma; A-9647), Avidin-D (Vector; A-2000) and Goat IgG anti-mouse IgG (total IgG fraction; Dept. Nephrology, Leiden University Medical Centre) were used to be labelled with biotin-Pt (cis[Pt(II)(en)(NH$_2$—(CH$_2$)$_2$—CO—(CH$_2$)$_2$—CO—(CH$_2$)$_2$—NH-biotin)CL](NO$_3$)) (KREATECH, ULK001), DNP-Pt (cis[Pt(II)(en)(NH$_2$—(CH$_2$)$_6$—NH-DNP)CL](NO$_3$)) (KREATECH, ULK003), Rhodamine-Pt (cis[Pt(II)(en)(NH$_2$—(CH$_2$)$_6$—NH-rhodamine)CL](NO$_3$)) (KREATECH, ULK101) and dGreen-Pt (cis[Pt(II)(en)(NH$_2$—(CH$_2$)$_6$—NH-dGreen)CL](NO$_3$)) (KREATECH, ULK301).

For each labelling of BSA and IgG, 250 µg protein in 250 µl PBS was mixed with 250 µl water containing 125 µg labelling reagent (protein to label ratio=1:0.5). When needed the volume was adjusted to 0.5 ml with distilled water. The reaction was allowed to proceed for 16 hrs at 37° C. Unbound labelling reagents were removed by gel filtration (SephadexG25, PD10; APB) with TBS/0.05% Tween 20 as eluent. DNP-Pt labelling of avidin-D was chosen to optimise labelling of proteins with none or non-accessible cysteine and methionine amino acids. Avidin-D was labelled at different protein:label ratios and at fixed ratios in 75 mM and 500 mM Na-phosphate-, TrisHCl- or Na-carbonate buffers with pH varying from 7 to 10. Protein concentrations during labelling remained 0.5 mg/ml, whereas label-Pt reagent concentrations varied between 0.25 to 0.75 mg/ml.

Fluorochrome to protein ratios (F/P ratio) as well as DNP to protein ratios (D/P ratio) were calculated by measuring the absorption at the fluorochrome absorption maximum (DNP: 363 nm, dGreen: 507 nm and rhodamine: 521 nm). A correction factor is introduced which adjusts the measurement for cis-platinum contributions at a particular wavelength and protein concentrations are determined using BCA reagent (Pierce; 23225). Calculating protein concentrations at 280 nm is disrupted by A280 nm contributions of the Pt reagent and can not be used. F/P-ratio formulas were then extracted using UV/VIS spectroscopy and Platinum flameless atomic absorbance spectroscopy (Pt-FAAS). Pt-FAAS was used to determine the number of protein-bound platinum compounds, which provided an accurate measurement of bound fluorochromes or DNP-molecules. The formulas used to calculate F/P and D/P-ratios are listed in Table 2.

TABLE 2

Formulas used to calculate fluorochrome to protein and DNP to protein ratios

| BSA-DNP: | IgG-DNP: | Av-DNP: |
|---|---|---|
| 3.78 × A363 [BSA] | 11.67 × A363 [IgG] | 5.5 × A363 [Avidin] |
| BSA-Rhod: | IgG-Rhod: | Av-Rhod: |
| 1.29 × A521 [BSA] | 3.63 × A521 [IgG] | 1.95 × A521 [Avidin] |
| BSA-dGreen | IgG-dGreen: | Av-dGreen: |
| 1.66 × A507 [BSA] | 3.85 × A507 [IgG] | 2.37 × A507 [Avidin] |

Table 3 shows that BSA and IgG contain more platinum bound fluorochromes compared to avidin-D. In case of Rhodamine-Pt: BSA contains 1 fluorochrome/16.6 kD, IgG has 1 fluorochrome/19.5 kD and avidin 1 fluorochrome/82.5 kD. Furthermore, DNP-Pt and Rhodamine-Pt have comparable reactivity and both are more reactive than dGreen-Pt.

TABLE 3

F/P- and D/P-ratios obtained from labelling experiments

| protein | label | protein:label ratio (µg:µg) | labeling buffer | F/P ratio or D/P ratio |
|---|---|---|---|---|
| BSA | Rhodamine | 1:0.5 | 0.25 × PBS pH 7.4 | 4.0 |
|  |  |  | 0.5 × PBS | 4.1 |
|  |  |  | 1 × PBS | 3.6 |
|  | DNP | 1:0.5 | 0.5 × PBS | 6.1 |
|  | dGreen | 1:0.5 | 0.5 × PBS | 2.4 |
| Goat IgG | DNP | 1:0.5 | 0.5 × PBS | 8.4 |
|  | Rhodamine | 1:0.5 | 0.5 × PBS | 7.7 |
|  | dGreen | 1:0.5 | 0.5 × PBS | 3.9 |
| Avidin-D | DNP | 1:0.5 | 0.5 × PBS | 1.6 |
|  | Rhodamine | 1:0.5 | 0.5 × PBS | 0.8 |
|  | dGreen | 1:0.5 | 0.5 × PBS | 0.3 |
| Avidin-D | DNP | 1:0.5 | TrisHCl 500 mM: pH 7 | 0.2 |

TABLE 3-continued

F/P- and D/P-ratios obtained from labelling experiments

| protein | label | protein:label ratio (µg:µg) | labeling buffer | F/P ratio or D/P ratio |
|---|---|---|---|---|
| | | | 75 mM; pH 7 | 1.6 |
| | | | 75 mM; pH 8 | 1.4 |
| | | | 75 mM; pH 9 | 1.6 |
| Avidin-D | DNP | 1:0.5 | Na carbonate | |
| | | | 500 mM: pH 8 | 0.8 |
| | | | 500 mM; pH 9 | 1.2 |
| | | | 500 mM; pH 10 | 1.9 |
| | | | 75 mM; pH 8 | 1.6 |
| | | | 75 mM; pH 9 | 1.5 |
| | | | 75 mM; pH 10 | 2.0 |
| | | 1:1.0 | 75 mM; pH 10 | 2.4 |
| | | 1:1.25 | 75 mM; pH 10 | 2.9 |

Experiments performed to increase D/P-ratios for avidin labelling are also listed in Table 3. It is shown that increase in pH of the labelling solution from pH 7 to pH 10 hardly increases the D/P-ratio at low salt conditions. A significant increase is found when the same experiment is performed at high salt conditions, however, a maximum D/P-ratio of 2 was found that could not be raised by varying salt or pH conditions. Increase of the label-Pt concentration during labelling was found to increase D/P-ratios further.

Example 4

Normal goat serum and serum of a goat immunised with mouse IgG, were labelled with DNP-Pt (cis[Pt(II)(en)(NH$_2$—(CH$_2$)$_6$—NH-DNP)CL](NO$_3$)) at a total protein to DNP-Pt ratio of 2:1 (w/w) for 16 hrs at 37° C. Mouse IgG was immobilised on a micro titre plate in a dilution series of coating concentrations of 0, 0.1, 0.3, 1, 3, 10, 30, 100, 300 and 1000 ng/ml per well. After this coating step the plates were rinsed with PBS-0.05% Tween 20 for three successive times and finally post-coated with 125 µl PBS/2% casein/3% BSA for 30 minutes at 37° C.

Next serum was diluted in maleic acid buffer (Roche Diagnostics) to a solution with a protein concentration of 0.5 ng/µl. Next 100 µl of labelled serum was added to the immobilised mouse IgG and was allowed to react for 60 min at 37° C. The micro titre plate was washed with 1×PBS-0.05% Tween 20 followed by an 1 hour incubation at 37° C. with an HRP labelled anti-DNP antibody (#NEN 7-1-99) diluted in maleic buffer. Unbound anti DNP-HRP was removed by 3 washes with 1×PBS-0.05% Tween 20, 1 min. each. Next, 100 µl TMB substrate, diluted in a citrate-phosphate buffer pH 5.3, was added to the wells and allowed to react in the dark for 30 min at room temperature (20-22° C.). To stop the reaction 100 µl of 1N H$_2$SO$_4$ was added. Absorption at 450 nm was determined as a measure for the anti Mouse IgG—labelled according to the invention—bound to Mouse IgG. The results are shown in FIG. 3. In contrast to the non-immunised goat serum the experiment with the immunised goat serum showed a signal of bound anti DNP, indicating that anti-mouse IgG has specifically bound to mouse IgG.

This experiment was repeated with biotin as the marker instead of DNP and anti-biotin instead of anti-DNP. Similar results were observed.

Example 5

Micro titre plates (MB, 762070, Griener) were coated with either Rabbit anti-humane IgG (DAKO, A0424), Rabbit anti-humane IgA (DAKO, A0092), Rabbit anti-humane IgM (DAKO, A0426), Rabbit anti-humane IgD (DAKO, A0093), or Rabbit anti-humane IgE (DAKO, A0094). Each antibody was dissolved in 1×PBS at a concentration of 10 µg/ml. The micro titre plates were coated with 100 µl overnight at room temperature. Next, the plates were rinsed with rinsing buffer (0.15 M NaCl, 4.9 mM Na$_2$HPO$_4$.2H$_2$O, 1.2 mM KH$_2$PO$_4$, 0.05% Tween 80, 0.005% thimerasol) and post coated with 150 µl 1×PBS, 2% casein, 3% BSA (30 min at 37° C.). Untreated whole human serum, at various dilution rates ranging from 1:250 up to 1:9·10$^5$ (in serum dilution buffer: 0.1 M Tris pH 7, 0.15 M NaCl, 1% BSA, 2% casein, 0.05% Tween 80, 0.025% thimerasol), was added (100 µl) to the anti-humane IgG and anti-humane IgA coated plates and incubated for one hour at 37° C. The wells were rinsed thoroughly and the detection limit established by using anti-humane IgG-HRP (DAKO, P-214/stock solution: 1:20 dilution in Stabilzyme Select (Surmodics), finally 1:100 diluted in serum dilution buffer) and anti-humane IgA-HRP (DAKO, P-216/1:35 dilution in Stabilzyme Select (Surmodics), finally 1:100 diluted in serum dilution buffer) conjugates and TMB substrate according to standard procedures.

The same untreated whole humane serum sample was labelled by adding DNP-Pt (cis[Pt(II)(en)(NH$_2$—(CH$_2$)$_6$—NH-DNP)CL](NO$_3$)) in a total protein to DNP-Pt ratio of 4:1 (w/w) and allowing the mixture to react overnight at room temperature. Next, the sample was diluted, added to the plates (100 µl/well), and incubated as above. Detection limit was determined by using anti-DNP-HRP conjugate (#NEN 7-1-99, 1:1000 dilution in serum dilution buffer; 100 µl/well; 1 hour at 37° C.) and TMB substrate (30 min. at room temperature).

The results were as follows:

| Entity | Classical sandwich ELISA | DNP-Pt format |
|---|---|---|
| IgG | 1:3.10$^5$ | 1:2.10$^5$ |
| IgA | 1:8.10$^4$ | 1:4.10$^4$ |
| IgM | n.a. | 1:2.10$^4$ |
| IgD | n.a. | 1:2.10$^3$ |
| IgE | n.a. | 1:2.10$^3$ |

All subclasses were shown to maintain their antigen binding capacity.

Example 6

The effect of ammonium sulphate was evaluated. First proteins were precipitated with either 50, 100, 200 or 400 µl of a saturated (NH$_4$)$_2$SO$_4$ solution (30 min on ice-30 min room temperature-centrifugation). The supernatant was separated from the precipitate. The precipitates were dissolved to a 0.5 mg/ml concentration in 0.5×PBS (without dialysis). The protein concentration was determined with BCA reagens (Pierce, see above). Next, the re-dissolved precipitate was labelled with DNP-Pt (cis[Pt(II)(en)(NH$_2$—(CH$_2$)$_6$—NH-DNP)CL](NO$_3$)) at a 4:1 ratio (w/w) for 4 hrs at 50° C. The results are shown in FIG. 4.

Also, the supernatants, transferred to new tubes, were labelled with DNP-Pt. To 0.5 mg protein (in the supernatant) 0.125 of DNP-Pt (cis[Pt(II)(en)(NH$_2$—(CH$_2$)$_6$—NH-DNP)CL](NO$_3$)) was added. The mixture was allowed to react for 4 hrs at 50° C. The results are shown in FIG. 5.

The results demonstrate that a method according to the invention can be used to label either a entity that has been precipitated in ammonium sulphate or an entity that is dissolved in an ammonium sulphate solution without need for remove any excess ammonium sulphate. The latter is not possible with standard labelling moieties, e.g. HNS-esters.

Example 7

In this example differential labelling is demonstrated by making use of fluorescence resonance energy transfer (FRET). The bio-organic molecule of choice is microperoxidase. Microperoxidase mp-11 (Sigma M6765) consists of 11 amino acids with two N reactive sites (lysine and histidine) and two S-reactive sites (cysteine). The full length sequence of mp-11 is: valine-glutamine-lysine (N)-cysteine (S)-alanine-glutamine-cysteine (S)-histidine (N)-threonine-valine-glutamine. Mp-11 was dissolved in 0.5×PBS (pH 7.2) at a concentration of 1 mg/ml. A aliquot of this solution (0.25 mg) was labelled with Flu-ULS at a 1:0.25 ratio in 0.5×PBS (final volume 499.5 µl) at 50° C. for 4 hours. The fluorescein labelled mp-11 solution was purified over a PD-10 column (APB, nr. 17-0851-01). Prior to the purification of the solution the column was rinsed three times with 5 ml 0.5×PBS. The fluorescein labelled mp-11 solution was analysed on a Ultrospec 4000 spectrophotometer (APB) Subsequent, fluorescein labelled mp-11 was labelled with rhodamine-ULS (ratio 1:0.25). Labelling was allowed to take place overnight at 4° C. Next, the solution was purified and analysed as described above.

The results are presented in FIG. 6. The data show that mp-11 is labelled with fluorescein (A470 FAM 50) and rhodamine (A510 FAM 50 Rho 4). An elevated rhodamine specific emission was obvious when the double labelled mp-11 was illuminated at 470 nm (this is the excitation wavelength of fluorescein) (A470 FAM 50 Rho 4). After excitation fluorescein transfers sufficient energy to the nearby rhodamine leading to fluorescence of rhodamine at 570 nm without direct excitation of rhodamine at 510 nm, this is FRET.

Example 8

Bovine serum albumin (BSA) was labelled with cis or trans rhodamine-Pt at pH 4 or 7. BSA was dissolved in 1×PBS (phosphate buffered saline, pH=7.4) at an amount of 3%. Small aliquots of this solution (3.3 µl) were labelled according the following scheme: (a) plus 25 µl rhodamine cis-Pt (cis[Pt(11)(en)(NH$_2$—(CH$_2$)$_6$—NH-rhodamine)CL](NO$_3$)) of a 1 mg/ml stock solution in 0.075 M NaAC/citrate buffer pH 4 (final volume 1 ml); (b) plus 12.5 µl Rhodamine trans-Pt (trans[Pt(II)(NH$_3$)$_2$(NH$_2$—(CH$_2$)$_6$—NH-rhodamine)CL](NO$_3$)) of a 2 mg/ml stock solution in 0.075 M NaAC/citrate buffer pH 4 (final volume 1 ml); (c) same as (a) but in 0.5× PBS pH 7; (d) same as (b) but in 0.5×PBS pH 7. In all cases the protein to label ratio is 1:0.25. Labelling took place at 50° C. for 4 hours. Thereafter the labelled BSAs were column purified. Visual evaluation of the samples clearly showed no coloured solution in (b) and (d) whereas (a) and (c) were coloured (c stronger then a).

Example 9

The effect of soft transition metals was evaluated in order to control further the differential labelling conditions. A ten fold excess of N-acetyl methionine (final conc. 2 mM) or N-acetyl histidine (final conc. 2 mM) was added to a solution containing either DNP-Pt (final conc. 0.2 mM) or Rho-Pt (final conc. 0.2 mM) in 10 mM sodiumphosphate pH 8 and 20 mM NaCl. To each solution either 0, 1, 2, or 5 equivalents of CdCl$_2$ or K$_2$PdCl$_4$ was added to study the influence of the presence of soft transition metals on reaction rates of marker-Pt compounds with S-reactive sites and N-reactive sites containing amino acids, respectively. The reactions were performed at 37° C. It should be noted that the pH dropped upon addition of the soft transition metal. This was observed for all soft transition metals used in this experiment. The drop in pH was the most pronounced for palladium and the least for cadmium. The disappearance of label-Pt was chosen as a measure and the samples lacking an additional soft transition metal (e.g. Pd, Cd, . . . ) served as controls. The relative changes measured in samples containing such additional soft transition metal(s) is a measure for the effect on the presence and concentration of such compound(s) on the labelling characteristics of N or S-reactive site containing amino acids. The results are presented in Table 4. The results show that labelling of methionine is very fast. This finding is in agreement with data presented above. Addition of considerable amounts of cadmium diminishes the reaction rate only slightly. However addition of palladium significantly inhibits the reaction in a concentration dependent manner. Labelling of histidine is quite slow, and decreases when cadmium is added. A 5 fold excess of cadmium with respect to histidine, prevented labelling to occur in the first place. Palladium seems to speed up the reaction with histidine when present at low concentration, at higher concentrations the reaction is slowed down. However these changes in reaction rate might not solely be due to the presence of a soft transition metal, or mixtures thereof, but also in part be due to changes in pH. Palladium has also an effect on labelling of both S-reactive site (e.g. methionine) and N-reactive site (e.g. histidine) containing amino acids, but more so on methionine. This offers an excellent opportunity to selectively diminish sulfur labelling.

Example 10

Bovine serum albumin (BSA, Sigma; A-9647) was dissolved in either 20 mM phosphate buffer pH 8 or 20 mM sodium acetate buffer pH 4 at a concentration of 5 mg/ml. To aliquots of these solutions was added Flu-Pt, Rho-Pt, Flu-NHS (Molecular Probes, C-6164, dissolved in DMSO at a concentration of 10 mg/ml) or Rho-NHS (Molecular Probes, C-6123, dissolved in DMSO at a concentration of 5 mg/ml) at a ten fold excess. The labelling reaction was allowed to take place over night at 37° C. All samples were purified by column purification (PD10) and analysed spectrophotometrically according to standard procedures. The results showed hardly any labelling at low pH for the Flu-NHS label whereas the Flu-Pt label displayed a significant higher F/P ratio. Note that the baseline Flu-NHS value is mainly attributable to non specific binding of the label (negative charge) to the protein (positive charge). Both labels yielded comparable F/P ratios at neutral pH matching the Flu-Pt value at low pH. Similar results were obtained with rhodamine with the exception that the Rho-Pt value was lower compared to the Rho-NHS value at low pH. In this case the data corresponding to the low pH experiment are actual baseline values representing no or very little labelling. This finding might at least in part be explained as a result of the overall net charge of the labelling compound in view of the charge of the protein.

This example demonstrates the successful use of different labelling technologies and potential electrocstatic interactions contributing to the scope of the present invention.

Example 11

Epidermal Growth Factor (EGF, Sigma; E9644) was dissolved in 50 mM phosphate buffer pH 8 at a concentration of 1 mg/ml. Ten fold excess of Flu-NHS (Molecular Probes, C6164; dissolved in DMSO at a concentration of 10 mg/ml) or Flu-Pt (KREATECH, ULK004) was added to aliquots of the EGF solution. The labelling reaction was allowed to take place overnight at 30° C. and 37° C. for the Flu-NHS and Flu-Pt markers, respectively. Next, the samples were purified by column purification (PD10) and analysed spectrophotometrically according to standard procedures. The results showed a F/P ratio of 0.07 and 0.28 for the Flu-NHS and Flu-Pt markers, respectively. EGF does not contain lysine and therefor is not a preferred target for NHS labelling. The terminal amino group serves as the only potential labelling site for a NHS complex. A significant higher F/P ratio was achieved for the Flu-Pt complex under similar conditions.

TABLE 4 t½ values from labelling reactions containing soft transition metals

| | | DNP-Pt | Rho-Pt |
|---|---|---|---|
| Methionine | | | |
| No soft transition metal | | 15 min | 15 min |
| CdCl$_2$ | 1 equivalent | 60 min (pH 7) | 60 min (pH 7) |
| | 2 | 60 min (pH 6) | 60 min (pH 6) |
| | 5 | 60 min (pH 4.5) | 60 min (pH 4.5) |
| K$_2$PdCl$_4$ | 1 equivalent | ≈100 hours (pH 7) | |
| | 2 | ∞(pH 5) | |
| | 5 | ∞(pH 3) | |
| Histidine | | | |
| No soft transition metal | | 3 hours | 3 hours |
| CdCl$_2$ | 1 equivalent | 15 hours (pH 7) | 15 hours (pH 7) |
| | 2 | 50 hours (pH 6) | 25 hours (pH 6) |
| | 5 | ∞(pH 4.5) | ∞(pH 4.5) |
| K$_2$PdCl$_4$ | 1 equivalent | 2 hour (pH 7) | |
| | 2 | ∞(pH 6) | |
| | 5 | ∞(pH 3) | |

We claim:

1. A method for differentially forming a complex of a platinum compound and an entity or at least one entity of a mixture of two or more entities, the method comprising:
   forming a complex of a platinum compound and an entity, said entity comprising one or more sulphur-containing reactive sites and one or more nitrogen-containing reactive sites, wherein said platinum compound is reacted with said entity such that substantially only nitrogen containing reactive sites are linked to said platinum compound; or
   forming a complex of a platinum compound and at least one entity of a mixture of two or more entities, said at least one entity or said entities together comprising one or more sulphur-containing reactive sites and one or more nitrogen-containing reactive sites, wherein said platinum compound is reacted with said at least one entity or said entities together, such that substantially only nitrogen containing reactive sites are linked to said platinum compound,
   wherein said sulphur containing site or sites are first differentially shielded by a shielding moiety and thereafter said platinum compound is differentially linked to the one or more nitrogen containing reactive sites;
   wherein said entity or said entities are selected from the group consisting of amino acids, peptides, oligopeptides, polypeptides, proteins, immunoglobulins, enzymes, synzymes, phospholipids, glycoproteins, nucleic acids, nucleosides, nucleotides, oligonucleotides, polynucleotides, peptide nucleic acids, peptide nucleic acid oligomers, peptide nucleic acid polymers, amines and aminoglycosides; and
   wherein said shielding moiety is a trans-platinum compound.

2. The method according to claim 1, wherein the shielding moiety is selectively removed from the shielded reactive site, after the platinum compound has been reacted such that said platinum is differentially linked to said entity.

3. The method according to claim 1, wherein said method comprises:
   differentially shielding, by means of a shielding moiety, sulfur-containing reactive site or sites of at least one entity of a mixture of two or more entities, said entity or entities together comprising one or more sulphur-containing reactive sites and one or more nitrogen-containing reactive sites;
   forming a complex of a platinum compound and at least one entity of a mixture of two or more entities, said at least one entity or said entities together, comprising one or more shielded sulphur-containing reactive sites and one or more nitrogen-containing reactive sites;
   wherein said platinum compound is reacted with said at least one entity such that substantially only nitrogen-containing reactive sites are linked to said platinum compound.

* * * * *